(12) United States Patent
Bradley

(10) Patent No.: US 6,490,486 B1
(45) Date of Patent: Dec. 3, 2002

(54) IMPLANTABLE CARDIAC STIMULATION DEVICE AND METHOD THAT MONITORS DISPLACEMENT OF AN IMPLANTED LEAD

(75) Inventor: Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 243 days.

(21) Appl. No.: 09/709,698

(22) Filed: Nov. 9, 2000

Related U.S. Application Data

(60) Provisional application No. 60/200,141, filed on Apr. 27, 2000.

(51) Int. Cl.[7] .............................. A61N 1/04; A61N 1/18
(52) U.S. Cl. ............................. 607/28; 607/4; 607/122; 600/374
(58) Field of Search ........................... 607/5, 9, 17, 19, 607/4, 28, 27, 119, 121, 122, 123; 600/374, 375, 509, 510

(56) References Cited

U.S. PATENT DOCUMENTS

| | | | | |
|---|---|---|---|---|
| 5,143,090 A | * | 9/1992 | Dutcher et at. ............. 607/121 |
| 5,431,692 A | * | 7/1995 | Hansen et al. ................ 607/27 |
| 5,466,254 A | * | 11/1995 | Helland ....................... 607/123 |
| 5,476,485 A | * | 12/1995 | Weinberg et al. ............. 607/28 |
| 5,607,455 A | | 3/1997 | Armstrong ....................... 607/8 |
| 5,755,742 A | | 5/1998 | Schuelke et al. ............. 607/27 |
| 5,814,088 A | | 9/1998 | Paul et al. .................... 607/28 |
| 5,944,746 A | | 8/1999 | Kroll ............................ 607/27 |
| 6,129,746 A | * | 10/2000 | Levine et al. ................. 607/27 |
| 6,157,859 A | * | 12/2000 | Alt ................................ 607/4 |
| 6,249,700 B1 | * | 6/2001 | Alt .............................. 607/19 |
| 6,327,499 B1 | * | 12/2001 | Alt ................................ 607/4 |

* cited by examiner

Primary Examiner—Willis R. Wolfe

(57) ABSTRACT

An implantable cardiac stimulation device and method that monitors displacement of a cardiac lead implanted in a heart. The device includes an impedance measurement circuit that generates a template representing the impedance measured using the lead over a cardiac cycle of the patient's heart. The impedance measurement circuit generates subsequent impedance measurement signals, which are then compared to the template to derive a comparison factor. The comparison factors are stored in a memory and are indicative of lead displacement. A telemetry circuit transmits the comparison factors to a non-implanted receiver for analysis of lead displacement.

29 Claims, 3 Drawing Sheets

IMPLANTABLE CARDIAC STIMULATION DEVICE AND METHOD THAT MONITORS DISPLACEMENT OF AN IMPLANTED LEAD

This application claims the benefit of U.S. Provisional Application No. 60/200,141, filed Apr. 27, 2000.

FIELD OF THE INVENTION

The present invention generally relates to an implantable cardiac stimulation device. The present invention more particularly relates to a device and method for use with such a device for monitoring displacement of an implanted cardiac lead.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads, which are implanted within the heart. The electrodes are positioned within the right side of the heart, either the right ventricle or right atrium, or both, for making electrical contact with their respective heart chamber. Conductors within the leads couple the electrodes to the device to enable the device to deliver the desired therapy.

Traditionally, therapy delivery had been limited to the right side of the heart. The reason for this is that implanted electrodes can cause blood clot formation in some patients. If a blood clot were released from the heart's left side, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy from or to the left heart. These lead structures and methods avoid direct electrode placement within the left atrium and left ventricle of the heart by lead implantation within the coronary sinus, the great vein, or a lateral vein of the heart. As is well known, the coronary sinus passes closely adjacent the left atrium, extends into the great vein adjacent the left ventricle and then continues adjacent the left ventricle towards the apex of the heart via a lateral vein or the great cardiac vein.

It has been demonstrated that electrodes placed in the coronary sinus and a left ventricular vein may be used for left atrial pacing, left ventricular pacing, and cardioversion and defibrillation. These advancements enable implantable cardiac stimulation devices to address the needs of a patient population with left ventricular dysfunction and congestive heart failure which would benefit from left heart side pacing, either alone or in conjunction with right heart side pacing (multi-chamber pacing).

Since the benefit of multi-chamber pacing (bi-ventricular pacing or bi-atrial pacing) is dependent upon appropriate chamber synchronization and/or appropriate activation sequencing, the maintenance of proper placement of the pacing electrodes to pace the left side of the heart is paramount. Thus, it is desirable for an implantable cardiac stimulation device to have a system, which can identify if the left heart lead placement is unstable or has shifted.

SUMMARY OF THE INVENTION

The present invention therefore provides an implantable cardiac stimulation device and method for monitoring displacement of a cardiac lead implanted in a heart, such as a cardiac lead implanted in the left heart. In accordance with the present invention, a template is generated representing the impedance of the lead over a discrete time period, such as a cardiac cycle of the heart. Thereafter, at spaced apart times, subsequent lead impedance measurement signals are generated and compared to the lead impedance measurement template from which a comparison factor is derived. The comparison factors are indicative of relative displacement of the implanted cardiac lead.

The comparison factors may be stored in a memory over time and conveyed by a telemetry circuit to a non-implanted receiver for analysis. The comparison factors may be generated by employing template matching or feature extraction techniques.

Either all of the comparison factors or selected ones of the comparison factors may be stored in the memory. The selected ones of the comparison factors to be stored may be those factors, which have a value greater than a predetermined factor.

When a comparison factor is stored in memory, other data may also be stored along with the comparison factor. Such data may include the date and time of the comparison, the patient's heart rate, the device mode, the posture of the patient, and/or portions of the digitized impedance waveforms. If the comparison factor is greater than the predetermined factor, a further template may be generated. Subsequent comparisons may then be made to all of the generated templates and corresponding comparison factors may be generated. The foregoing provides comprehensive data for the physician to track displacement of the implanted lead should displacement of the lead occur.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
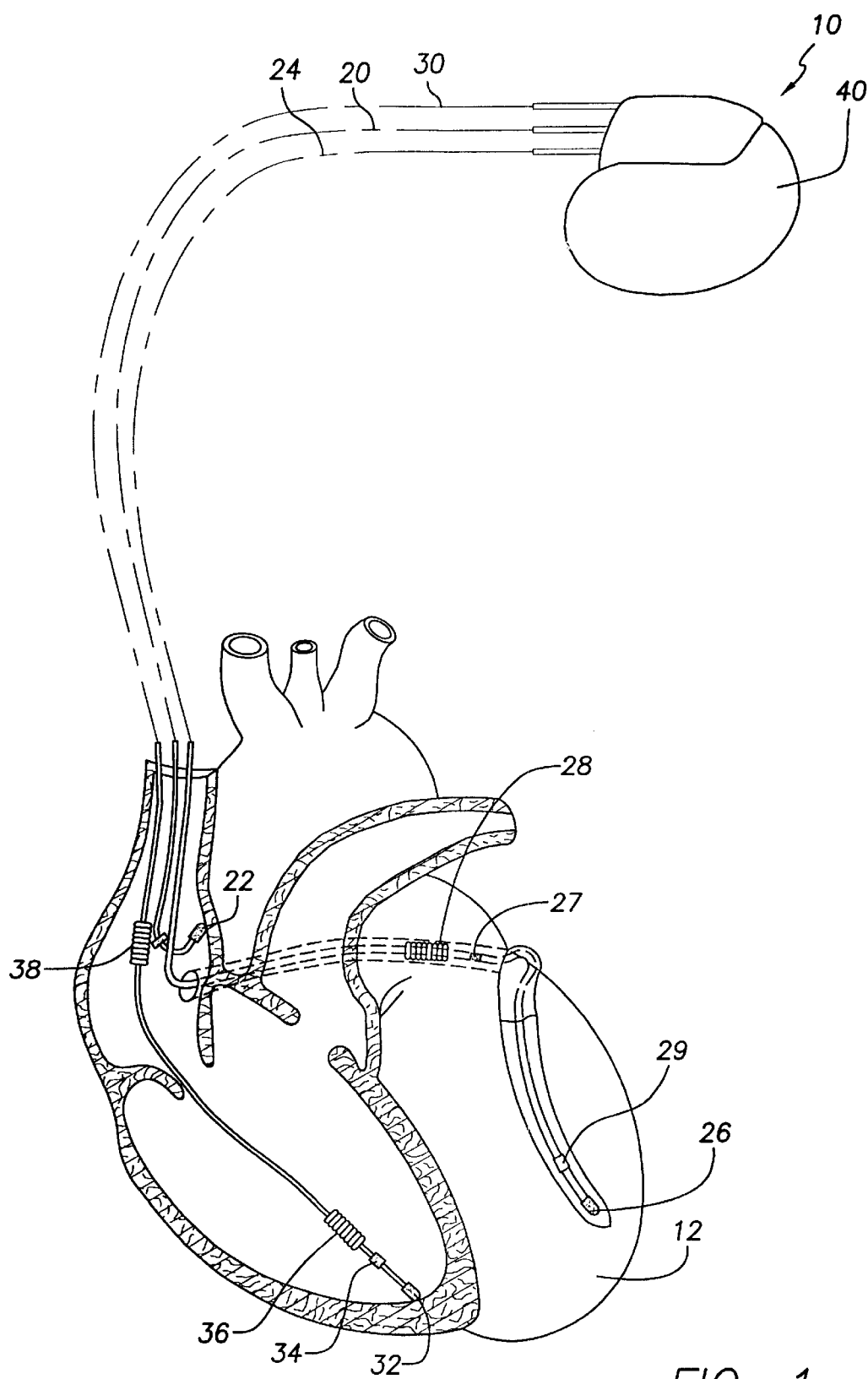
FIG. 1 is a simplified diagram illustrating an implantable stimulation device embodying the present invention shown in electrical communication with at least three leads implanted into a patient's heart for delivering multi-chamber stimulation and shock therapy.

As shown in FIG. 1, there is a stimulation device 10 embodying the present invention in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os, so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8/1999, entitled "A Self-Anchoring, Steerable Coronary Sinus Lead" (Pianca et al. still pending and U.S. Pat. No. 5,466,254, "Coronary Sinus Lead with Atrial Sensing Capability" (Helland), which patent application and patent, respectively, are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
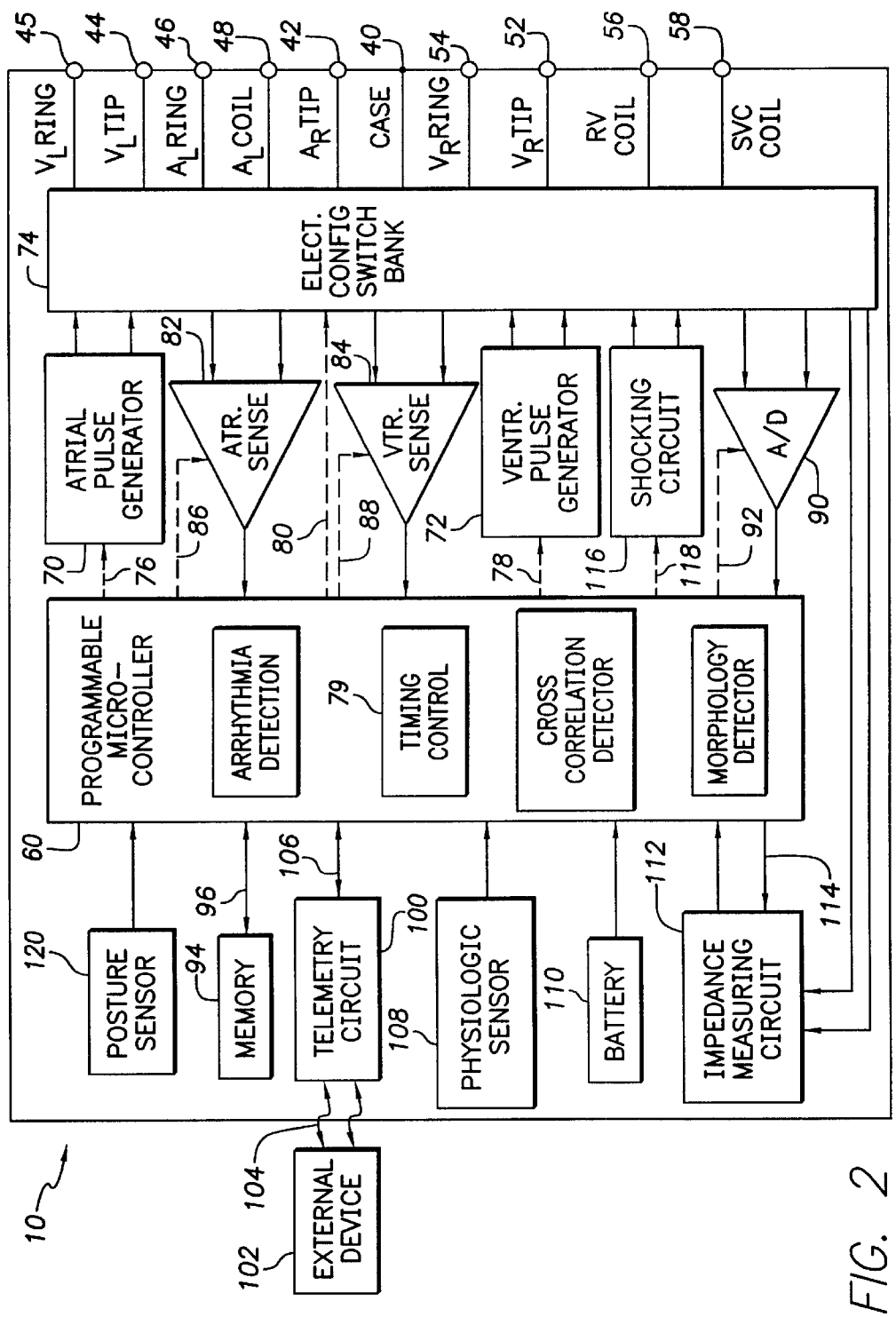
FIG. 2 is a functional block diagram of the device of FIG. 1 illustrating the basic elements thereof for providing cardioversion, defibrillation and pacing stimulation in four chambers of the heart and for monitoring lead displacement in accordance with a preferred embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation and monitoring displacement of any one of the implanted leads in accordance with the present invention. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 45, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively. Additionally, a left ventricular ring terminal 45 may be coupled to a left ventricular ring electrode 29.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry or processor, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry which is used to control the timing of such stimulation pulses (e.g., pacing rate, atrio-ventricular (AV) delay, interatrial (A—A) delay, or ventricular interventricular (V—V) delay, pacing mode, etc.) as well as to keep track of the timing of refractory periods, PVARP intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, is able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, pacing mode, etc.) determine how the atrial and ventricular pulse generators, 70 and 72, generate stimulation pulses.

The stimulation device additionally includes a battery 110, which provides operating power to all of the circuits shown in FIG. 2. For the stimulation device 10, which employs shocking therapy, the battery must be capable of operating at low current drains for long periods of time (preferably less than 10 $\mu$A), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 employs lithium/silver vanadium oxide batteries, as is currently true for most (if not all) such devices.

The device 10 further includes a posture sensor 120. The posture sensor detects the posture of the patient between a fully upright position and a supine position. To that end, the sensor 120 may include accelerometers, which detect acceleration in three mutually transverse directions. The raw signals from the sensor 120 are provided to the microcontroller 60, which may generate two different control signals. A first control signal may be a logical "1" if the patient is in an upright position and a logical "0" if the patient is in a supine position. A second control signal may be a multiple-bit binary fractional factor between 0 and 1 representing the posture of the patient. For example, the fractional factor may vary from 0, representing the patient in a supine position, to 1, representing the patient in a fully upright position. One such posture sensor is fully described in copending U.S. application Ser. No. 09/457,451, filed Dec. 8, 1999, entitled "An AC/DC Multi Axis Accelerometer for Determining Patient Activity and Body Position," still pendings which application is owned by the assignee of the present invention and incorporated herein in its entirety by reference.

It is the primary function of the device 10 to function as an implantable cardioverter/defibrillator (ICD) device. That is, it must detect the occurrence of an arrhythmia and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11–40 joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36 or as part of a split electrical vector using the SVC coil electrode 38 or the left atrial coil electrode 28 (e.g., using the RV electrode as common).

Cardioversion shocks are generally considered to be of low to moderate energy level (so as to minimize pain felt by the patient) and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, and in accordance with the present invention, the device 10 includes an impedance measuring circuit 112 which is enabled by the microcontroller 60 by a control signal 114. While the impedance measuring circuit 120 has many known conventional uses, it finds particular employment, in accordance with the present invention, for monitoring displacement of any one of the implanted leads 20, 24, and 30. For purposes of this description, however, it will be assumed that displacement of the coronary sinus lead 24 is to be monitored.

To the above end, the impedance measuring circuit 112 is coupled to the left ventricular tip terminal 44 and to the case terminal 40 by the switch bank 74. It is then commanded by the microcontroller 60 by control signal 114 to generate an impedance measurement signal using lead 24 over a cardiac cycle of the heart. The microcontroller 60, as the impedance measurement signal is generated by the impedance measurement circuit 112, stores the impedance measurement signal in the memory 94 as a template. This is preferably accomplished at or recently following the time of implant of the device 10 and leads. The microcontroller 60 also stores in memory 94 the template along with the noted pacing parameters and the pacing conditions at the time which the template was measured. For example, if the pacemaker's base rate is programmed to 70 beats per minute (bpm) but the patient's intrinsic rate is 82 bpm, the device is effectively inhibited from pacing. This status information is stored in the device along with the template. The device 10 is then programmed to cause the microcontroller 60 to initiate subsequent impedance measurements at spaced apart times, such as, at substantially the same time each day. This is to help ensure that the template is generated while the patient is in a relatively similar hemodynamic state for each measurement. Preferably, the device 10 is programmed to initiate the subsequent impedance measurements at night when the patient is normally in a supine position and at rest. Also, the subsequent impedance measurements are preferably made with identical pacing parameters and sensed pacing conditions as those present during the creation of the template. If such conditions are not present at the scheduled time for impedance measurements, then the device goes into an alert mode, awaiting recreation of similar conditions to trigger the subsequent impedance measurement.

Each subsequent impedance measurement is also preferably made to generate an impedance signal over a cardiac cycle of the patient's heart. The subsequent impedance signals are then stored in the memory 94 and compared to the template by the microcontroller to generate a comparison factor.

The comparisons may be determined by template matching, a technique well known in the art. The template stored in memory may be aligned with the subsequent impedance measurement signals using fiducial points, a technique also well known in the art. Once aligned, the template and signal are compared. The comparison may be based upon areas of corresponding deflections or amplitudes of corresponding deflections. Further, the areas and amplitudes of the recently acquired impedance measurement signals may be assigned positive or negative values based upon the polarity of the corresponding deflections.

The foregoing comparison may be quantified by deriving, from the comparison, a comparison factor value or score. The comparison score may, for example, be expressed as a percentage, ranging between 0 and 100. A score of 100 percent represents a perfect match and a score of 0 percent represents a perfect mismatch. The comparison score may be based upon comparative deflection amplitudes, areas, and polarity, calculated by template matching methods such as point-by-point subtraction and sum-of-differences, true correlation coefficient calculations, etc.

The comparison scores are then stored by the microcontroller 60 in the memory 94. To that end, the microcontroller 60 may establish a comparison log in the memory 94 for storing the comparison scores. All of the comparison scores or selected ones of the comparison scores may be stored. For example, only those comparison scores less than a predetermined score may be stored to conserve storage space. Along with each stored comparison score, the microcontroller 60 may also store other data useful in analysis such as, for example, the corresponding date, time of day, patient's heart rate, device mode, and/or the patient's posture as determined by the posture sensor 120. Additionally, the microprocessor may store the actual digitized impedance waveforms (including the template) along with the comparison scores. This storage may be made programmable by the physician (e.g., store all waveforms; store those with score less than 0.7; store no waveforms, etc.).

Over time the comparison scores will be indicative of lead displacement. The telemetry circuit 100 may be used to transmit the stored comparison scores and other related data to the external device 102 for analysis.

In accordance with a further aspect of the present invention, if a comparison score is less than a predetermined value, the microcontroller 60 may command the impedance measuring circuit to generate an additional impedance template. Subsequent impedance measurement signals may then be compared to both templates to generating corresponding comparison scores for storage in separate comparison logs in memory 94. Any number of such additional templates may be generated consistent with the storage space available in memory 94.

Figure 3:
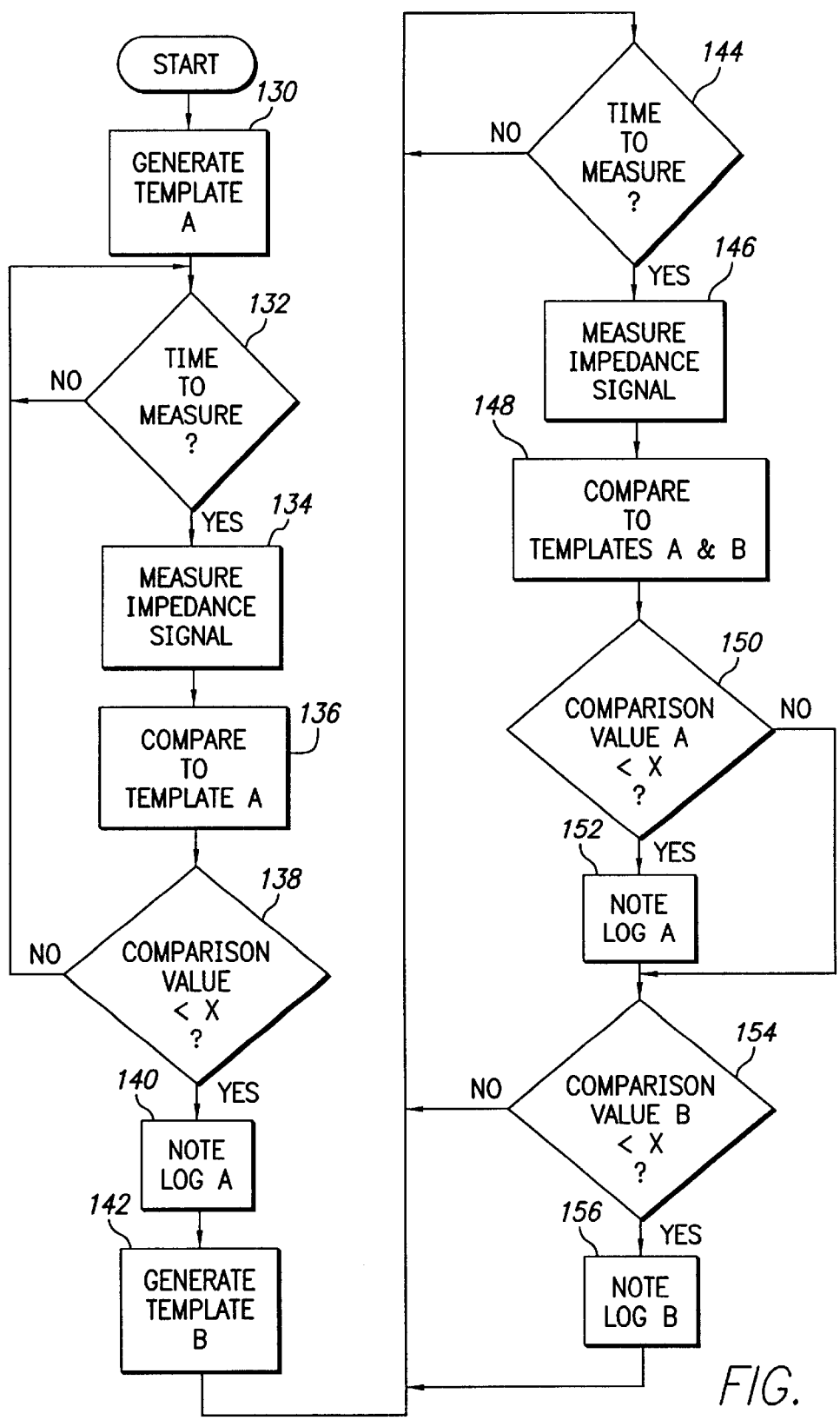
FIG. 3 is a flow chart describing an overview of the operation of the preferred embodiment of the present invention.

In FIG. 3, an exemplary flow chart is shown describing an overview of the operation and novel features implemented in the device 10 in accordance with the preferred embodiment of the present invention. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates at activity block 130 where a first impedance measurement template, template A, is generated and stored in the memory 94. This template, template A, is preferably generated and stored in the memory at, or recently following, the time of implant of the device and its associated leads. Following the generation of template A, the microcontroller 60 waits until a programmed time for measuring the impedance. When a programmed time arrives to make such a measurement as determined in decision block 132, the process proceeds to activity block 134 where a subsequent impedance measurement is made. In implementing activity block 134, the impedance measuring circuit 112 is commanded by the microcontroller 60 to generate an impedance signal using, for example, lead 24 over a cardiac cycle of the patient's heart. The impedance measurement signal generated in accordance with activity block 134 is immediately stored in the memory 94 by the microcontroller 60. The process then advances to activity block 136.

In activity block 136, the microcontroller 60 compares the most recently stored impedance measurement signal to the first template, template A and generates a corresponding comparison value. The comparison value is preferably generated in a manner as previously described. The process then advances to decision block 138 where the microcontroller 60 determines if the comparison value generated in activity block 136 is less than a predetermined value, X. If the comparison value is greater than the predetermined value, the process returns to decision block 132 to await the next programmed time for an impedance measurement. However, if the comparison value is less than the predetermined value, the process advances to activity block 140 where the microcontroller 60 notes the comparison value in the log, log A, corresponding to the template A and other relevant data such as the date and time of day of the comparison, the patient's heart rate, the device mode, and the patient's posture as sensed by the posture sensor 120.

The process then advances to activity block 142 where an additional template, template B, is generated. Activity block 142 is preferably implemented in a similar manner as the implementation of activity block 130, by the microcontroller 60 being responsive to the comparison value being less than the predetermined value to command the impedance measuring circuit 112 to generate an additional impedance measurement signal for storage in the memory 94 as template B. The microcontroller then waits until the next programmed time to make an impedance measurement.

When the next programmed time to make an impedance measurement arrives as determined in decision block 144, the microcontroller commands the impedance measuring circuit 112 to generate another impedance measurement signal over a cardiac cycle of the patient's heart in accordance with activity block 146. The impedance measurement signal generated in activity block 146 is immediately stored by the microcontroller in the memory 94.

Next, in activity block 148, the microcontroller 60 compares the stored impedance measurement signal generated in activity block 146 to all of the templates, in this case, templates A and B. It then completes the comparisons by generating separate comparison values, comparison value A and comparison value B corresponding to the respective templates, A and B.

The process then advances to decision block 150 where the microcontroller determines if the comparison value A is less than the predetermined value. If it is, the microcontroller 60 advances to activity block 152 to note the comparison value in log A of the memory 94 along with the other desired relevant corresponding data. Once activity block 152 is completed or if it is determined in decision block 150 that the comparison value A is greater than the predetermined value, the process advances to decision block 154 where the microcontroller determines if the comparison value B is greater than the predetermined value. If it is not, the process then returns to decision block 144 to await the arrival of the next program time to make a lead impedance measurement. However, if the comparison value B is greater than the predetermined value, the microcontroller, then in activity block 156, stores the comparison value B in the log B of memory 94 which corresponds to comparisons made to template B and then returns to decision block 144.

The foregoing process repeats as programmed until the process is terminated by the physician or other medical personnel by way of the external device 102. When it is time to analyze the results of the comparisons, the external device 102 may be utilized to cause the telemetry circuit 100 of the device 10 to transmit to the external device 102 the stored comparison values along with the other related corresponding data. The physician or other medical personnel will then have a comprehensive set of data to analyze to determine if lead displacement has occurred and to the extent of the lead displacement.

While the invention has been described by means of specific embodiments and applications thereof, it is understood that numerous modifications and variations could be made thereto by those skilled in the art without departing from the spirit and scope of the invention. It is therefore to be understood that within the scope of the claims the invention may be practices otherwise than as specifically described herein.

What is claimed is:

1. In an implantable cardiac stimulation device that monitors displacement of a cardiac lead implanted in a heart, the device comprising:

an impedance measurement circuit that generates an impedance measurement signal representing impedance measured using the implanted lead over a discrete time period;

a memory for storing the impedance measurement signal to provide an impedance template, wherein the impedance measurement circuit periodically generates subsequent impedance measurement signals; and a processor programmed to compare the subsequent impedance measurement signals to the impedance template and to generate comparison factor values from the comparisons, the comparison factor values being indicative of relative displacement of the implanted cardiac lead.

2. The device of claim 1 wherein the processor is further programmed to store at least selected ones of the comparison factor values and wherein the device further includes a telemetry circuit configured to transmit the stored comparison factors to an external receiver.

3. The device of claim 1, wherein the processor is programmed to cause the impedance measurement circuit to generate the subsequent impedance signals at substantially the same time of day, using the same programmed pacing parameters and verifying that the pacing conditions are substantially similar to the conditions present when the template was created.

4. The device of claim 1 wherein the discrete time period is a cardiac cycle of the heart.

5. The device of claim 1 wherein the processor is further programmed to store the comparison factor values in the memory.

6. The device of claim 5 wherein the processor is further programmed to store in the memory with each comparison factor value at least one of a corresponding date, time, heart rate, device mode, patient posture, and a number of the digital samples derived from the impedance measurement.

7. The device of claim 1 wherein the processor is further programmed to maintain a comparison log and to store comparison factor values in the comparison log which are less than a predetermined factor value.

8. The device of claim 7 wherein the processor is further programmed to store in the comparison log with each stored comparison factor value at least one of a corresponding date, time, heart rate, device mode, patient posture, and a number of the digital samples derived from the impedance measurement.

9. The device of claim 1 wherein the processor is further programmed to cause the impedance measurement circuit and memory to provide at least one additional impedance template when a comparison factor value is less than a predetermined factor value.

10. The device of claim 9 wherein the processor is programmed to compare each subsequent impedance measurement signal to each impedance template.

11. The device of claim 10 wherein the processor is further programmed to provide a comparison factor value for each corresponding comparison.

12. In an implantable cardiac stimulation device for monitoring displacement of a cardiac lead implanted in a heart, the device comprising:

impedance template means for providing a template representing variations in impedance measured using the implanted lead over a predefined time period;

impedance measurement means for generating impedance signals representing impedance measured using the implanted lead;

comparison means for comparing each of the impedance signals to the template and for providing corresponding comparison values, the comparison values being indicative of lead displacement;

memory means for storing at least selected ones of the comparison values; and telemetry means for transmitting the comparison values to a non-implanted receiver.

13. The device of claim 12 wherein the impedance measurement means generates the lead impedance signals at substantially the same time each day using the same programmed pacing parameters and verifying that the pacing conditions are substantially similar to the conditions present when the template was created.

14. The device of claim 12, wherein the predefined time period is a cardiac cycle of the heart.

15. The device of claim 12 wherein the memory means includes a comparison log for storing the comparison values.

16. The device of claim 15 further including means for determining and storing in the comparison log with each stored comparison value at least one of a corresponding date, time, heart rate, device mode, patient posture and a number of the digital samples derived from the impedance measurement.

17. The device of claim 12 wherein the memory means includes a comparison log for storing comparison values which are less than a predetermined value.

18. The device of claim 17 further including means for determining and storing in the comparison log with each stored comparison value at least one of a corresponding date, time, heart rate, device mode, patient posture, and a number of the digital samples derived from the impedance measurement.

19. The device of claim 12 wherein the impedance template means is responsive to a comparison value being less than a predetermined value for providing at least one additional impedance template.

20. The device of claim 19 wherein the comparison means compares each impedance signal to each impedance template.

21. The device of claim 20 wherein the comparison means provides a comparison factor value for each corresponding comparison.

22. In an implantable cardiac stimulation device, a method of monitoring displacement of a cardiac lead implanted in a heart, the method comprising the steps of:

generating and storing a template representing impedance of the implanted lead at a predetermined time;

at spaced apart times, providing an impedance signal representing impedance of the implanted lead;

comparing each impedance signal to the template to generate a corresponding comparison value;

storing in a memory at least selected ones of the comparison values, the comparison values be related to lead displacement; and conveying the comparison measures to an external receiver for analysis.

23. The method of claim 22 wherein the memory includes a comparison log and wherein the storing step includes the step of storing the at least selected ones of the comparison values in the comparison log.

24. The method of claim 22 further including the step of determining and storing in the memory, with each stored comparison value, at least one of a corresponding date, time, heart rate, device mode, patient posture, and a number of digital samples derived from the impedance measurement.

25. The method of claim 22 wherein the storing step includes the step of storing only the comparison values less than a predetermined value.

26. The method of claim 22 wherein the step of providing an impedance signal is performed at substantially the same time each day, using the same programmed pacing parameters and further including the step of verifying that pacing conditions are substantially similar to the conditions present when the template was created.

27. The method of claim 22 wherein the generating and storing and the providing steps are performed during a complete cardiac cycle of the heart.

28. The method of claim 22 further including the step of generating and storing an additional template representing impedance of the implanted lead when a comparison value is less than a predetermined value.

29. The method of claim 28 wherein the comparing step includes the step of comparing each impedance signal to each template and generating a comparison value for each comparison.

* * * * *